United States Patent [19]
Reinhardt

[11] Patent Number: 5,919,836
[45] Date of Patent: Jul. 6, 1999

[54] PRIMER FOR PREPARING A TOOTH CAVITY FOR A COMPOSITE FILLING

[75] Inventor: Klaus-Jürgen Reinhardt, Münster, Germany

[73] Assignee: Ernst Mühlbauer KG, Germany

[21] Appl. No.: 08/968,983

[22] Filed: Nov. 12, 1997

[30] Foreign Application Priority Data

Nov. 14, 1996 [DE] Germany .......................... 196 47 140
Dec. 9, 1996 [DE] Germany .......................... 196 51 121

[51] Int. Cl.$^6$ ....................................................... A61K 6/08
[52] U.S. Cl. .......................... 523/118; 523/116; 524/417; 524/547; 526/277; 526/278; 433/228.1
[58] Field of Search ................................... 523/116, 118; 524/417, 547; 526/277, 278

[56] References Cited

U.S. PATENT DOCUMENTS

| | | | |
|---|---|---|---|
| 4,368,043 | 1/1983 | Yamauchi et al. ...................... | 523/118 |
| 4,966,934 | 10/1990 | Huang et al. ........................... | 524/547 |
| 5,270,351 | 12/1993 | Bowen .................................... | 523/116 |
| 5,739,177 | 4/1998 | Ohno et al. ............................. | 526/277 |

*Primary Examiner*—Andrew E. C. Merriam
*Attorney, Agent, or Firm*—Medlen & Carroll, LLP

[57] ABSTRACT

The invention relates to the use of a mixture which comprises:

a) 1–5 weight % (wt. %) of phosphoric acid;
b) 10–90 wt. % of phosphoric acid mono- or di- methacrylates;
c) 1–15 wt. % of phosphoric acid trimethacrylates; and
d) 3–50 wt. % of diphosphates having between two and four methacrylate ester groups;

for the preparation of a composition for preparing a tooth surface for joining with a dental composite material. Using the composition according to the invention, a tooth cavity can be prepared in one step for laying a composite filling. A very high adhesive strength is achieved between the tooth matter and the composite material.

22 Claims, No Drawings

PRIMER FOR PREPARING A TOOTH CAVITY FOR A COMPOSITE FILLING

The invention relates to the use of a certain mixture for the preparation of a composition for preparing a tooth surface for joining with a dental composite material, and to a correspondingly prepared composition.

Before tooth cavities are filled with a polymerizable composite material based on plastics, the tooth matter (dentine or enamel) must be pretreated in order to ensure good adhesion of the composite to this. A good join between the tooth and filling is important, since all the known composite materials shrink in particular during the initial phase of the polymerization. If adhesion is inadequate, gaps form at the edges, bacteria can penetrate into the gaps at the edges and can cause secondary caries and/or can damage the pulp.

It is known from prior public use to carry out this pretreatment in four steps before laying the filling. The tooth enamel is first superficially etched with an acid etching solution, which as a rule comprises phosphoric acid. Where appropriate, another etching liquid must be used for etching dentine. In the next step, the etching solution is washed off. In the third step, a primer is applied to the etched surface and cured (if appropriate by means of light). Primers as a rule comprise polymerizable acids and are described, for example, in DE-A 35 36 077, U.S. Pat. No. 4,514,342, U.S. Pat. No. 4,388,421 and DE-A 40 32 882. In a fourth step, a so-called bond is applied to the cured primer, and as a rule must also be cured with light. The bonding systems used are as a rule methacrylates, in particular hydrophilic methacrylates (for example hydroxyethyl methacrylates). As a rule, bonding systems additionally comprise a small proportion of acids, in particular polymerizable acids. The bond should offer a base for the composite material subsequently to be laid, into which base this material can be incorporated by polymerization.

The object of the invention is to provide a composition for preparing a tooth surface, such as, for example, a tooth cavity, for joining with a dental composite material which is easier and less time-consuming to use and nevertheless ensures a good join between the tooth matter and the composite filling.

According to the invention, to prepare such a composition, a mixture is used which comprises:

a) 1–5% by weight of phosphoric acid;
b) 10–90% by weight of phosphoric acid mono- and/or diesters of the formula

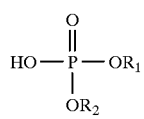

wherein

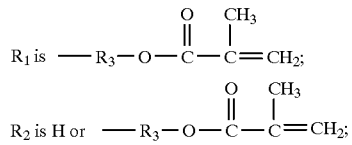

$R_3$ is chosen from the group consisting of alkylene groups, alkylenoxy groups having one or more alkylenoxy units and alkylene or alkylenoxy groups substituted by one or more hydroxyl groups;

c) 1–15% by weight of phosphoric acid triesters of the formula $$O=P(OR_1)_3 \quad (II)$$

with the abovementioned meaning for $R_1$; and d) 3–50% by weight of diphosphates of the formula

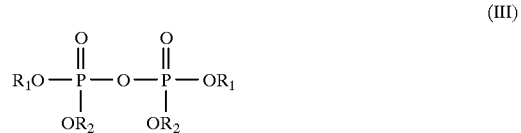

with the abovementioned meanings for $R_1$ and $R_2$ wherein $R_2$ in formula (III) can be identical or different.

The invention enables a tooth surface to be prepared in a single step for laying a composite filling. The composition according to the invention comprises a mixture of phosphoric acid, a main content of phosphoric acid mono- and/or diesters, and furthermore phosphoric acid triesters and diphosphates. The low phosphoric acid content is used for the preparatory etching of the tooth surface. The phosphoric acid esters used according to the invention are molecules of which the acid hydroxyl groups can join chemically with the calcium of the tooth surface. The partly esterified phosphoric acid group is joined to a methacrylate group via an alkylene or alkylenoxy group (which optionally carries hydroxyl groups) which serves as a spacer. The methacrylate groups can partly polymerize and thus form a film on the tooth surface, into which the composite material can copolymerize. The phosphoric acid ends of the molecules can penetrate into dentine tubuli, because of their good mobility, and in this way improve the mechanical adhesion to the tooth surface.

The percentage data in claim 1 are based on the so-called resin content of the mixture, which in the case of a solvent-free mixture is 100%. If a solvent is added, it decreases according to the amount of solvent added.

Phosphoric acid esters linked with methacrylate groups via spacers have not previously been considered as a combined etching agent and primer and, if appropriate, adhesive (bond) for tooth surfaces. One reason for this lies in the fact that such phosphoric acid derivatives are not stable in the pure form and therefore cannot be stored. The adhesive strength of such pure phosphoric acid derivatives is low, as is also explained below with the aid of a comparison example.

Surprisingly, it has been found that the mixture according to the invention of phosphoric acid mono-, di- and triesters and diphosphates have both a good storage stability and a very high adhesive strength. Etching, priming and, if appropriate, bonding can be carried out in a single process step using this mixture.

In the context of the invention, the term "preparing a tooth surface for joining with a dental composite material" used in claim 1 includes both etching of the tooth surface and priming. Priming comprises establishing a good join between the primer and tooth surface, inter alia by penetration of the phosphoric acid ends located at the spacer sections of the molecules into the dentine tubuli of the tooth matter. The primer has the effect of good mechanical adhesion to the tooth surface. The steps of etching and priming, which are carried out separately in the prior art, can be carried out according to the invention in a single step. The term mentioned preferably also additionally includes so-called bonding. Bonding refers to the provision of a good adhesive base for subsequent incorporation of the composite material by polymerization. Primers used in prior art frequently do not offer a sufficient base for this incorporation by polymerization, so that it is necessary in addition to apply a bond in order to produce sufficient mechanical adhesion to the composite. In accordance with the invention this is preferably not necessary; the mixture used renders additional bonding superfluous and itself forms a good adhesion base for the composite material.

The spacer group in the phosphoric acid derivatives is preferably selected from the group consisting of alkylene groups having 2–4 C atoms, ethylenoxy or propyleneoxy groups which can consist of up to 4 glycol units (ethylene or propylene glycol units), and alkylene groups having 2–4 C atoms which are substituted by one or two hydroxyl groups.

Preferred spaces are ethylene or propylene groups, and also a group of the formula

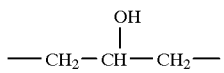

an isomer thereof.

In the mixture according to the invention, the main content comprises phosphoric acid mono- and diesters, and makes up preferably 30–90% by weight, and more preferably 40–80% by weight, based on the resin content. A ratio of 20–35% by weight of phosphoric acid monoesters and 25–45% by weight of phosphoric acid diesters is furthermore preferred. The phosphoric acid content of the mixture is preferably 1–3% by weight.

The mixture according to the invention can be applied directly to the tooth surface to be treated, but a solvent can additionally be added. Suitable solvents are acetone, ethanol, isopropanol, THF and water. Acetone, ethanol and water are preferred solvents. The content of solvent or solvents in the total mixture is preferably 30–95% by weight.

It is possible to use the mixtures according to the invention without an added polymerization initiator. In this case, the polymerization is initiated starting from the composite material, after the filling has been laid. However, a polymerization initiator, preferably a photoinitiator, can be added. Photoinitiators are familiar to the expert and are described, for example, in FR-A 2 156 769 and GB-A 1 408 265. They can be, for example, aromatic ketones or a mixture of diketones and tertiary amines. Camphorquinone, if appropriate in combination with a tertiary amine, is preferred as the photoinitiator, and is initiated by visible light. A photoinitiator which is initiated by UV light is, for example, 1,2-diphenyl-2,3-dimethoxymethanone.

The invention is explained below with the aid of an embodiment example and a comparison example.

EXAMPLE 1

25 g of phosphoric acid trichloride are dissolved in 100 ml of THF. 15 g of HEMA are added dropwise in portions, with exclusion of moisture and while cooling. The mixture is stirred for three days, 2 g of water are then added and the mixture is stirred for a further 24 hours. The solvent and the HCl formed are removed in vacuo.

The reaction mixture is analyzed by means of $^{31}$P-NMR spectroscopy. It has the following composition:

2% of phosphoric acid, 25% of phosphoric acid monoester, 35% of phosphoric acid diester, 7% of phosphoric acid triester and 31% of diphosphate.

All the percentage data are percentages by weight.

25 g of this reaction mixture are dissolved in 75 g of acetone. 0.1 g of camphorquinone and 0.05 g of triethanolamine are then added.

Comparison Example 1

25 g of bis(2-methacryloxyethyl) phosphate are dissolved in 75 g of acetone, and 0.1 g of camphorquinone. and 0.05 g of triethanolamine are added.

The adhesion values which a composite material achieves on bovine dentine using the mixture of Example 1 or Comparison Example 1 are measured by the method described in ISO draft TR 11405. The following values result:

Example 1: 18 MPa

Comparison Example 1: 12 MPa

I claim:

1. A composition comprising: a) 1 to 5% phosphoric acid by weight; b) 10 to 90%, by weight, phosphoric acid esters selected from the group consisting of mono and diesters, wherein said phosphoric acid ester comprises the formula:

and wherein $R_1$ is

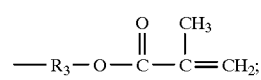

and wherein $R_2$ is

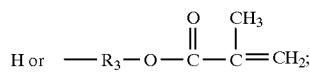

and wherein $R_3$ is selected from the group consisting of alkylene groups, alkylenoxy groups having at least one alkylenoxy unit, alkylene groups substituted by at least one hydroxyl group, and alkylenoxy groups substituted by at least one hydroxyl group; c) 1 to 15%, by weight, phosphoric acid triesters of the formula:

wherein $R_4$ is:

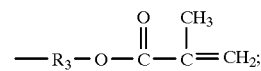

and d) 3 to 50%, by weight, of diphosphates of the formula:

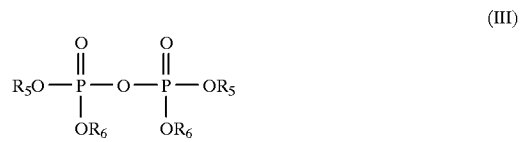

wherein $R_5$ is

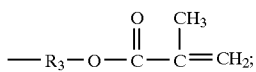

and $R_6$ is

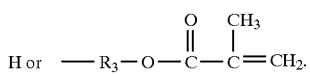

2. The composition of claim 1, wherein said $R_3$ is selected from the group consisting of alkylene groups having two carbon atoms, alkylene groups having three carbon atoms, alkylene groups having four carbon atoms, ethylenoxy groups of four or less glycol units, propylenoxy groups of four or less glycol units, alkylene groups having two carbon atoms and two or less substituted hydroxyl groups, alkylene groups having three carbon atoms and two or less substituted hydroxyl groups, and alkylene groups having four carbons and two or less substituted hydroxyl groups.

3. The composition of claim 1, wherein said $R_3$ is selected from the group consisting of ethylene, propylene groups, and

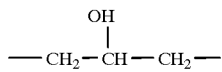

or an isomer thereof.

4. The composition of claim 1, wherein the proportion of said phosphoric acid esters is 30 to 90% by weight.

5. The composition of claim 1, wherein the proportion of said phosphoric acid esters is 40 to 80% by weight.

6. The composition of claim 1, wherein the proportion of said phosphoric acid monoesters is 20 to 35% by weight, and the proportion of said phosphoric acid diesters is 25 to 45% by weight.

7. The composition of claim 1, wherein said phosphoric acid comprises 1 to 3% of said composition.

8. The composition of claim 1, further comprising a solvent.

9. The composition of claim 8, wherein said solvent is 30 to 95% of said composition by weight.

10. The composition of claim 8, wherein said solvent is selected from the group consisting of ethanol, acetone, and water.

11. The composition of claim 1, further comprising a photoinitiator.

12. A method for preparing a tooth surface for joining with dental composite material comprising the steps of:

a) providing: i) a tooth surface, and ii) a composition comprising: a) 1 to 5% phosphoric acid by weight (wt.); b) 10 to 90% wt. phosphoric acid esters selected from the group consisting of mono and diesters, wherein said phosphoric acid ester comprises the formula:

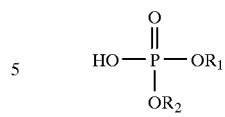

(I)

and wherein $R_1$ is

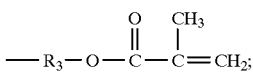

and wherein $R_2$ is

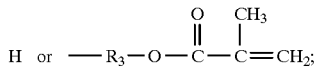

and wherein $R_3$ is selected from the group consisting of alkylene groups, alkylenoxy groups having at least one alkylenoxy units, alkylene groups substituted by at least one hydroxyl group, and alkylenoxy groups substituted by at least one hydroxyl group; c) 1 to 15% wt. phosphoric acid triesters of the formula:

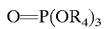

(II)

wherein $R_4$ is:

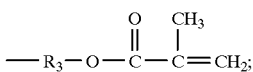

and d) 3 to 50% wt. of diphosphates of the formula:

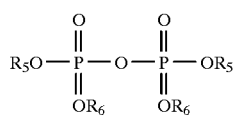

(III)

wherein $R_5$ is

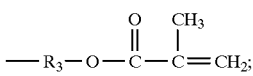

and $R_6$ is

and b) applying said composition to said tooth surface.

13. The method of claim 12, wherein said $R_3$ of said composition is selected from the group consisting of alkylene groups having two carbon atoms, alkylene groups having three carbon atoms, alkylene groups having four carbon atoms, ethylenoxy groups of four or less glycol units, propylenoxy groups of four or less glycol units, alkylene groups having two carbon atoms and two or less substituted hydroxyl groups, alkylene groups having three carbon atoms and two or less substituted hydroxyl groups, and alkylene groups having four carbons and two or less substituted hydroxyl groups.

14. The method of claim 13, wherein said $R_3$ of said composition is selected from the group consisting of ethylene, propylene groups, and

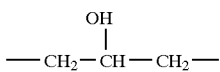

or an isomer thereof.

15. The method of claim 12, wherein the proportion of said phosphoric acid esters is 30 to 90% of said composition by weight.

16. The method of claim 12, wherein the proportion of said phosphoric acid esters is 40 to 80% of said composition by weight.

17. The method of claim 12, wherein the proportion of said phosphoric acid monoesters of said composition is 20 to 35% by weight, and the proportion of said phosphoric acid diesters of said composition is 25 to 45% by weight.

18. The method of claim 12, wherein said phosphoric acid comprises 1 to 3% of said composition.

19. The method of claim 12, wherein said composition further comprises a solvent.

20. The method of claim 19, wherein said solvent is 30 to 95% of said composition by weight.

21. The method of claim 19, wherein said solvent is selected from the group consisting of ethanol, acetone, and water.

22. The method of claim 12, wherein said composition further comprises a photoinitiator.

* * * * *

UNITED STATES PATENT AND TRADEMARK OFFICE
CERTIFICATE OF CORRECTION

PATENT NO. : 5,919,836
DATED : 07/06/99
INVENTOR(S) : Klaus-Jürgen Reinhardt *et al.*

It is certified that error appears in the above-identified patent and that said Letters Patent is hereby corrected as shown below:

On the title page, item [75], after "Inventor: Klaus-Jürgen Reinhardt, Münster, Germany", please insert "Rainer Lück, Tornesch, Germany."

Signed and Sealed this

Twenty-ninth Day of February, 2000

Attest:

Q. TODD DICKINSON

Attesting Officer

Commissioner of Patents and Trademarks